(12) United States Patent
Green et al.

(10) Patent No.: US 8,823,530 B2
(45) Date of Patent: Sep. 2, 2014

(54) SYSTEM AND METHOD FOR AUTO-CORRECTING AN AUTONOMOUS DRIVING SYSTEM

(71) Applicant: GM Global Technology Operations LLC, Detroit, MI (US)

(72) Inventors: Charles A. Green, Canton, MI (US); Jeremy A. Salinger, Southfield, MI (US); Omer Tsimhoni, Herzliya (IL); Eric L. Raphael, Birmingham, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 35 days.

(21) Appl. No.: 13/768,623

(22) Filed: Feb. 15, 2013

(65) Prior Publication Data

US 2014/0139341 A1 May 22, 2014

Related U.S. Application Data

(63) Continuation-in-part of application No. 13/678,652, filed on Nov. 16, 2012.

(60) Provisional application No. 61/560,874, filed on Nov. 17, 2011.

(51) Int. Cl.
*G08B 23/00* (2006.01)
*G08B 21/02* (2006.01)
*B60K 28/06* (2006.01)

(52) U.S. Cl.
CPC ............. *G08B 21/02* (2013.01); *B60K 28/06* (2013.01)
USPC ............................ 340/576; 340/439; 180/272

(58) Field of Classification Search
USPC ..................... 340/576, 575, 439; 180/272
See application file for complete search history.

(56) References Cited

U.S. PATENT DOCUMENTS

| | | | | |
|---|---|---|---|---|
| 5,694,116 | A * | 12/1997 | Kojima | 340/576 |
| 6,262,657 | B1 * | 7/2001 | Okuda et al. | 340/439 |
| 7,292,152 | B2 * | 11/2007 | Torkkola et al. | 340/576 |
| 7,987,030 | B2 | 7/2011 | Flores et al. | |
| 8,260,482 | B1 | 9/2012 | Szybalski et al. | |
| 2011/0241862 | A1 * | 10/2011 | Debouk et al. | 340/439 |

* cited by examiner

*Primary Examiner* — John A Tweel, Jr.
(74) *Attorney, Agent, or Firm* — Mark S. Cohen; Pearl Cohen Zedek Latzer Baratz LLP

(57) ABSTRACT

A method and system for driver attention management system may include means for closed-loop diagnostics. A convenience message may alert a driver of an item of interest to the driver. A sensor may detect the driver's response to the convenience message. Based on the response to the convenience message, the characteristics of an attentive response from the driver may be determined. The determined attentive response may be used by a driver attention management system. The driver attention management system may be able to diagnose errors in the sensors that are used in the driver attention management system. The driver attention management system may also be able to determine whether a driver is exercising sufficient supervisory control of a vehicle by determining whether the driver is attentively responding to prompts provided by the driver attention management system. The driver attention management system may be used in an autonomous or semi-autonomous driving system.

20 Claims, 7 Drawing Sheets

SYSTEM AND METHOD FOR AUTO-CORRECTING AN AUTONOMOUS DRIVING SYSTEM

CROSS-REFERENCE TO RELATED APPLICATION

This application is a continuation-in-part of U.S. patent application Ser. No. 13/678,652 filed Nov. 16, 2012, which claims priority under 35 U.S.C. §119(e) to U.S. provisional patent application Ser. No. 61/560,874, filed Nov. 17, 2011. The entire contents of these related applications are incorporated by reference in their entirety.

FIELD OF THE INVENTION

The present invention is related to methods and systems to interface with and influence a driver and the driver's supervisory role in an autonomous driving system such as a limited-ability autonomous driving (LAAD) system.

BACKGROUND

Vehicles may be equipped with limited-ability autonomous and/or semi-autonomous driving systems, embodiments, and/or features. Autonomous and semi-autonomous driving systems may provide automated driving controls that reduce the driver interaction required for operating the vehicle. Automated lane following systems for example, may be activated by the driver while the vehicle is in motion, and may maintain the vehicle position in a lane. LAAD systems may reduce driver fatigue and increase safety by maintaining the vehicle position with respect to the road, and other conditions relevant to driving, with reduced driver input, compared to manual driving.

Safety considerations may be taken into account when designing LAAD systems. In order to conform to safety requirements, LAAD systems may be overridden by the driver at any time. When the driver overrides the vehicle lane following system, for example, the system relinquishes full steering control of the vehicle to the driver. However, while a LAAD system is controlling the vehicle, the driver may forget or not realize that the LAAD lacks the ability to handle certain driving situations. Some systems employ driver monitoring systems and may also inform the driver of their attentiveness to the vehicle through a display or indicator. However, these displays may distract the driver and lower the driver's attentiveness to the driving task. Other systems similar to forward collision warning systems may attempt to attract a distracted driver's attention to the road, but may activate based only on external event triggers such as another fast approaching vehicle. A system may be needed that both avoids distracting the driver and increases the driver's attentiveness and control of the vehicle—a system that can operate constantly without regard to external triggering events, and activates only as necessary to maintain a minimum level of driver attention.

SUMMARY

A method and system for driver attention management system may include means for closed-loop diagnostics. A convenience message may alert a driver of an item of interest to the driver. A sensor may detect the driver's response to the convenience message. Based on the response to the convenience message, the characteristics of an attentive response from the driver may be determined. The determined attentive response may be used by a driver attention management system. The driver attention management system may be able to diagnose errors in the sensors that are used in the driver attention management system. The driver attention management system may also be able to determine whether a driver is exercising sufficient supervisory control of a vehicle by determining whether the driver is attentively responding to prompts provided by the driver attention management system. The driver attention management system may be used in an autonomous or semi-autonomous driving system.

BRIEF DESCRIPTION OF THE DRAWINGS

The subject matter regarded as the invention is particularly pointed out and distinctly claimed in the concluding portion of the specification. Embodiments of the invention, however, both as to organization and method of operation, together with objects, features, and advantages thereof, may best be understood by reference to the following detailed description when read with the accompanying drawings in which:

Figure 1:
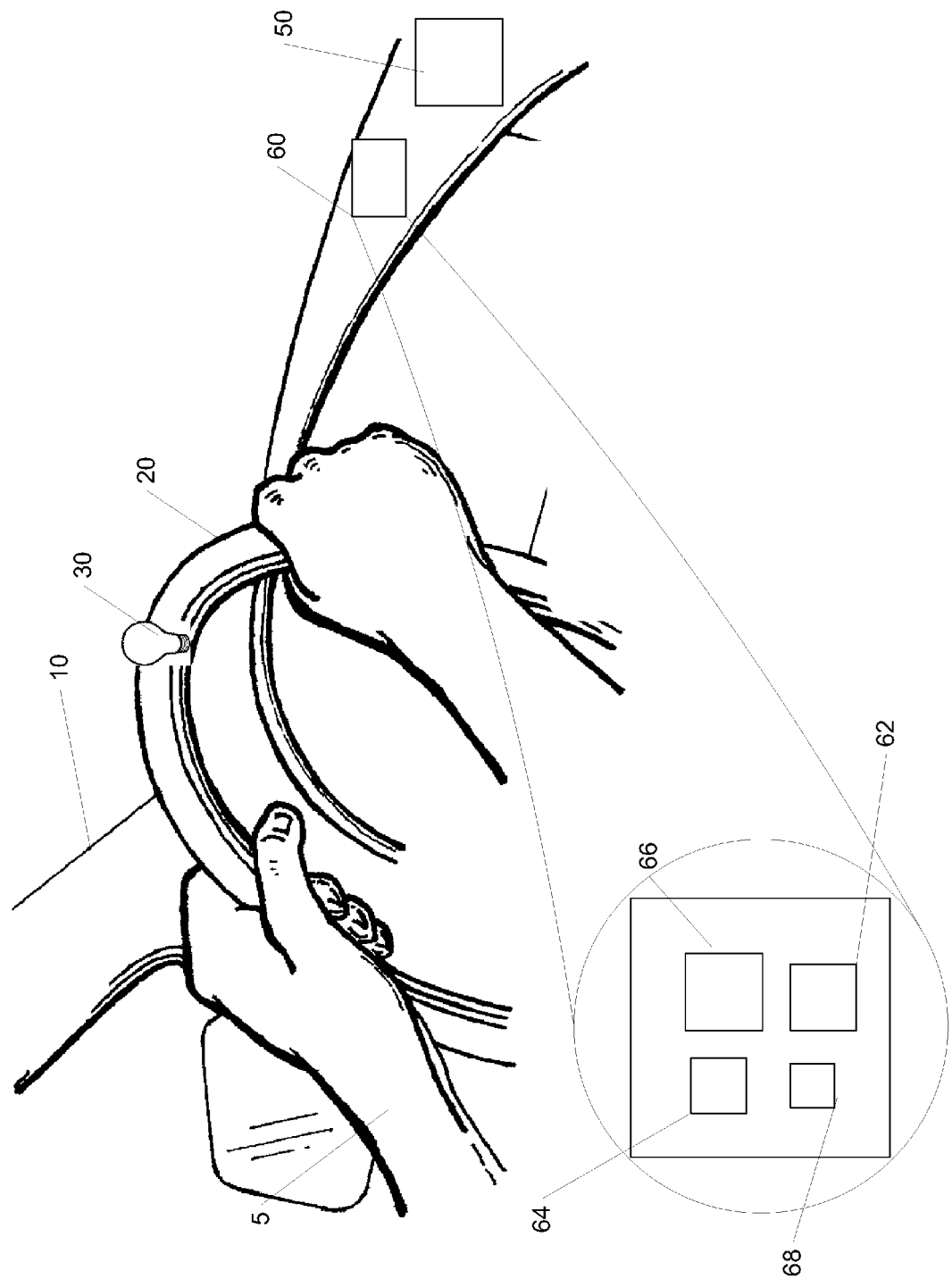
FIG. 1 is a schematic diagram of a vehicle with a system according to an embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Unless specifically stated otherwise, as apparent from the following discussions, throughout the specification discussions utilizing terms such as "processing," "computing," "storing," "calculating," "determining," "evaluating," "measuring," "providing," "transferring," "outputting," "inputting," or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

An autonomous driving system may be a driving system that includes one or more autonomous elements that control vehicle movement on a road, rendering the vehicle fully autonomous (e.g., no driver input or control required) or partially autonomous (e.g., some driver input or control required for safe driving). Limited-ability, autonomous, semi-autonomous, automated, or automatic driving control features (e.g., automated lane following, adaptive lane following, adaptive cruise control, etc.) may maintain or control the position and speed of a vehicle with respect to the road and other vehicles and obstacles on the road with reduced driver input (e.g., reduced or no driver steering wheel movement or accelerator and brake pedal control). In order to comply with safety requirements, however, the driver will need to monitor the performance of the system for safety, due to technological limitations of the sensor systems used by the automated control systems. Further, the driver may need to regain full control of the vehicle driving controls and deactivate or disengage the driving system. Additionally, in order to help the driver maintain a supervisory role, the driver may need to be reminded periodically of the driving conditions surrounding the vehicle.

A driver interface for a LAAD system may therefore be required to function during all driving scenarios to provide different levels of cues, reminders or prompts to the driver, such that the driver may maintain a supervisory role during the entire operation of the vehicle.

The driver may also need to regain control of the vehicle, for example, when a lane sensing driving system may make errors which cause the vehicle to depart the lane or road, to avoid an unexpected obstacle, when another vehicle swerves into the driver's lane, when an obstacle lies in front of the vehicle, when the vehicle comes into close proximity with a guardrail, the driver switches lanes, or in other circumstances that may require the driver's attention. The driver may also need to constantly stay in a supervisory role of the vehicle, independent of conditions outside or within the vehicle. A driver may be deemed to maintain supervision or sufficient control of a vehicle when the driver contemporaneously responds to a driving cue. The driving cue may be external or internal, and a contemporaneous response may be a response that is within seconds (e.g. 1, 2, 2.5, or 3 seconds).

According to some embodiments of the present invention, a LAAD system, or any other driving system known in the art, may be equipped with a steering wheel that produces or includes lights, or is lit (entirely, or a portion thereof) by a light internal to the steering wheel, or in other embodiments, by a light that may be external to the steering wheel. In some embodiments, the steering wheel may be lit or produce light to indicate to the driver the level of autonomy or control employed by an automated driving system. In some embodiments, the steering wheel may be lit or produce light, to indicate to the driver the level of supervisory control necessary by the driver to operate the vehicle while the vehicle is employing a LAAD system, or another driving system known in the art.

Typically, the steering wheel may be lit or produce light, with a distinct color, pattern or colored pattern for each level of autonomy employed by the autonomous driving system. In some embodiments, the steering wheel may be lit or produce light, with a distinct color, pattern or colored pattern to indicate to the driver the level of supervisory control necessary to safely operate the vehicle while the vehicle is employing a LAAD system, or another driving system known in the art.

In some embodiments, the light illuminating the steering wheel may pulse, flash, or blink at varied intervals, or at different intensities, or consistent frequencies, in different spatial pattern, to indicate the level of autonomy employed by the LAAD system, or another driving system known in the art. The intervals and frequencies at which the light illuminates may produce apparent motion.

In some embodiments, the light illuminating the steering wheel may pulse, flash or blink at varied intervals or at different intensities or frequencies or different spatial patterns to indicate the level of supervisory control necessary on the part of the driver to operate the vehicle, while the vehicle is employing a LAAD system, or another driving system known in the art.

In some embodiments, the entirety of the steering wheel may be lit or produce light. In other embodiments, only a top portion of the steering wheel may be lit or produce light. This top portion of the steering wheel may be between 10 o'clock and 2 o'clock e.g., between 11 o'clock and 1 o'clock. Other ranges may be used.

In some embodiments, a vehicle may be equipped with a closed-loop driver visual attention management (DVAM) system. Typically, a closed-loop DVAM system may contain an emitter that emits or signals an alert to the driver. The emitter may be a light emitting device that may emit one or more brief flashes of light in the direction of the peripheral vision of the driver who may be looking away from the road. Typically, the light may be emitted for a short duration or time period, the light emitter configured such that the light emitter may no longer be emitting light by the time the driver responds to the light, and turns to look toward the light.

In some embodiments, the light may be configured such that the light is perceived to be emanating from the windshield of the vehicle. In other embodiments, the light emitter may be configured to emit light such that the driver sees a reflection of the light in the windshield. In other embodiments, the light may be perceived by the driver to be on the dashboard of the vehicle. In some embodiments, the light emitter may be configured to emit light such that the driver sees the reflection of the light on a component of the vehicle. In other embodiments, the light emitter may be configured so that the driver sees the actual light emitted by the light emitter. The light may be emitted from a dedicated light emitting component, or from an existing display, such as a Heads-Up Display that reflects off of the windshield.

Typically, the closed-loop DVAM system may further include sensors that detect whether the driver has looked toward the emitted light, or its reflection. These sensors may look at driver eye-gaze, driver head position, or both, or other characteristics that are indicative of the focus of the driver's visual attention.

In some embodiments, a vehicle may be equipped with a convenience messaging system that at a given interval, for example every 5 minutes (other intervals may be used) provides a tone, an audio message, visual message, an audiovisual message, or a tone and a message to the driver regarding road conditions, driving conditions, or other items that may be of interest to the driver. Other items of interest may include nearby or upcoming points of interest such as a rest area or food, or the quality of cellular reception in the vicinity, for example. The convenience messaging system may further omit messages, or increase the time between messages in case it has other indications that the driver is attentive to the driving task, or is moving their head in response to other alerts, for example.

In some embodiments, the convenience messaging system may be in communication with multiple sensors associated with the vehicle. Typically, the convenience messaging system, in response to changing road or driving conditions, or in response to other instances where it may be determined that the driver needs to take a more supervisory role, may provide a tone, a audio, visual or audiovisual message, or a tone and a message to the driver. Typically, the message may relate to the information collected by the sensors.

In some embodiments of the invention, the convenience messaging system may be a closed-loop system. After providing the tone or message or both the tone and message to the driver, the convenience messaging system may wait for a response from the driver. This waiting period may be between 3 and 5 seconds. Other ranges may be used. Typically, the response from the driver may include looking toward the source of the tone and/or message. In some embodiments, a sensor may determine whether the driver has looked toward the source of the tone or the message. In other embodiments, the convenience messaging system may require a response from the driver in the form of a positive affirmation. Typically, the positive affirmation may be a verbal response. In other embodiments the positive affirmation may be an action with the hands, arms, feet or other body part. The response could also include looking to the road following a look to the message, or another type of gaze pattern or signature. Audio sensors may be included to assess the driver's verbal response. In other embodiments, the affirmation may be a touch response to the steering wheel, the accelerator or a separate foot switch or elbow switch as are known in the art. Sensors may be included to assess the driver's response. In other embodiments, the affirmative response may include an interaction with a secondary vehicle system, including, but not limited to a radio system, an audio or entertainment system, a touch screen, a Bluetooth coupled cellular telephone or device, or a turn signal. In other embodiments, the affirmative response may be determined by a change in the driver's heart rate, breathing rate, temperature or other biological responses. Sensors may be included to assess the driver's response.

In some embodiments of the present invention, a vehicle may be equipped with a staged or sequenced alerting system, the system designed to assess a driver's current supervisory role in controlling the vehicle, and provide a staged range of intrusive or urgent cues or prompts configured to obtain a greater supervisory role by the driver of the vehicle. In some embodiments, the staged range of increasingly intrusive or urgent cues or prompts is configured to confirm the driver's current supervisory role in operating the vehicle.

In some embodiments, the convenience messaging system may work with the staged or sequenced alerting system, or any other kind of DVAM, as a closed-loop diagnostics system. The entire system may use the convenience messaging system to auto-correct the desired responses from the driver. Since a driver is much more likely to respond to convenience messaging than a prompt from a DVAM, the response to a convenience message may help to determine a general response from the driver that indicates attentiveness. The resulting determination of an attentive response may be used in the DVAM, to determine whether a driver has sufficient supervisory control of a vehicle. The attentive response may also be used to diagnose whether there are errors in the DVAM itself.

In some embodiments, a convenience messaging system may alert a driver of an item of interest to the driver. As described previously, an item of interest may include information on external driving conditions, such as traffic information or weather, and nearby destinations of interest, such as rest stops, restaurants, or gas stations. The driver may be likely to respond to the convenience message, because the message conveys information that the driver is interested in, or the message may assist with driving in general. The driver may respond by a variety of behaviors: head movement, eye movement, verbal responses, or interaction with the vehicle, such as clutching the steering wheel more firmly. Any of these behaviors may be deemed to be an attentive response. For example, if the convenience messaging system is located on the dashboard, the convenience message system may determine that the driver's most frequent response to the convenience message is glancing at the dashboard and changing grip on the steering wheel. The system may determine that these behaviors are an attentive response, i.e., the behaviors that indicate that the driver is attentive to driving and external conditions. The system may alternatively determine that these behaviors are NOT an attentive response, depending on the rules programmed into the convenience messaging system. During a prompting stage of the DVAM, the DVAM may look for these behaviors in determining whether the driver is sufficiently in control of the vehicle, or the DVAM may look for a similarity in the driver's response to its prompts and the characteristics of the determined attentive response.

In some embodiments, the DVAM may determine that one of its sensors is malfunctioning, based on the affirmative response determined by the convenience message system. For example, the convenience message may elicit or request a verbal response from the driver. The DVAM may require the same verbal response from the driver in response to its prompts. When the driver responds to the convenience message through the required verbal response, the DVAM may test the response as also affirming that the driver is exercising sufficient supervisory control of the vehicle. If the DVAM and the convenience message system fail to reach the same determination of an attentive response, the DVAM may diagnose its its speech sensor as malfunction. Other sensors on the DVAM may be used for diagnostics in accordance with embodiments of the invention, such as a head movement detector, eye movement detector, or other body movement detector.

Typically, the staged alerting system may be triggered if a driver monitoring system detects a less than adequate response from the driver in response to a cue or prompt, typically from the closed-loop DVAM system and the convenience messaging system. In some embodiments of the present invention, the staged alerting system may be triggered if the driver monitoring system determines that the driver's supervisory role in operating the vehicle is less than adequate given detected conditions by sensors in the vehicle and/or outside of the vehicle. In some embodiments, the staged alerting system may be triggered at a set interval. In some embodiments, the staged alerting system may be triggered if the current conditions—as determined by sensors associated with the vehicle, including RADAR systems, cameras and other sensors known in the art are or are about to go outside the bounds of operation of the LAAD system, or another driving system known in the art, and/or the LAAD system, or another driving system known in the art, needs input from the driver, or needs the driver to take greater than current control over the vehicle.

In some embodiments of the current invention, the staged alerting system initially provides one or more attention cues or prompts. For example, the staged alerting system may provide a brief flash of light in the direction of the peripheral vision of the driver from a light emitter (for example similar to what is described elsewhere with respect to the closed-loop DVAM system).

The staged alerting system may detect a response, or lack of response to the emitted light, similar to the detection of responses that are described with respect to the closed-loop DVAM system. If the staged alerting system determines that the driver does not respond to the one or more attention cues or prompts, or in some embodiments, if the staged alerting system detects that the response to the one or more attention cues or prompts is insufficient, given current conditions, then the staged alerting system may provide a more intrusive or urgent cue or prompt to the driver.

In some embodiments, the staged alerting system provides a short duration or time interval for a response to the cues or prompts, typically, this short interval for a response may be from 3 to 7 seconds. Other ranges may be used. In some embodiments, the staged alerting system may require a response indicative of the driver taking a greater role in controlling the vehicle; typically, this may include touching the steering wheel or the accelerator or brake pedals. In some embodiments, the staged alerting system may require a response from the driver indicating that the driver has taken full control of the vehicle, interacting with the accelerator and or brake pedals or moving the steering wheel. Other interactions involving secondary control systems in the vehicle, including interacting with the navigation system or global positioning system (GPS) system or the turn signals, or other secondary systems known in the art, may also be assessed by the staged alerting system in determining the appropriate response from the driver in response to cues or prompts.

In some embodiments, a more intrusive or urgent cue or prompt may include one or more non-visual cues or prompts. Typically, the non-visual cues or prompts may be a haptic cue or prompt from the driver's seat, steering wheel, other component of the vehicle, or a combination thereof. Haptic cues or prompts may include shaking or vibrating of the seat or the steering wheel or other cues or prompts known in the art. In some embodiments, the staged alerting system may also, in addition to the haptic cue or prompt, or instead of the haptic cue or prompt, provide an audible or other non-visual cue or prompt, as are known in the art. If the staged alerting system determines that the driver does not respond to the non-visual cue or prompt, or in some embodiments, if the staged alerting system detects that the response to the non-visual cue or prompt is insufficient, then the staged alerting system may provide a more intrusive or urgent cue or prompt to the driver.

In some embodiments, a more intrusive or urgent cue or prompt following a non-visual cue or prompt may include one or more speech or earcon (e.g., a brief, distinctive sound used to represent a specific event or convey other information) cues or prompts. Typically, a speech cue or prompt may include a direct command or question to the driver. In some embodiments, the speech or earcon cue or prompt may be generated through the speakers in the vehicle. In some embodiments, the speech or earcon cue or prompt may be generated through a cellular telephone that may be coupled to the vehicle, e.g., via a Bluetooth communication connection. Other audio outputs may be used as well. If the staged alerting system determines that the driver does not respond to the speech or earcon cue or prompt, or in some embodiments, if the staged alerting system detects that the response to the speech or earcon cue or prompt is insufficient, then the staged alerting system may provide a more intrusive or urgent cue or prompt to the driver. Additionally the vehicle's LAAD system, or another driving system known in the art, may not reengage unless the ignition in the vehicle is cycled from on to off to on again. In some embodiments, the vehicle's LAAD system may not reengage unless a predetermined time interval has passed.

In some embodiments, a more intrusive or urgent cue or prompt following a speech or earcon cue or prompt may include a reduction in the vehicle's speed. Typically, in a reduction of the vehicle's speed, the staged alerting system may disengage normal control of the LAAD system, or another driving system known in the art, and may further begin to slow or reduce the speed of the vehicle. In some embodiments, the reduction in speed may be limited, for example, to between 10 and 30 miles per hour (mph) below the prevailing traffic speed. Other ranges may be used. In some embodiments, the staged alerting system may move the vehicle to the side of the road and stop, or pulse the brakes as the vehicle is slowed, or bring the vehicle to a complete stop in the road. The system may further temporarily prevent the driver from accelerating the vehicle, for example, for a few seconds or minutes (e.g., 1 second, 5 seconds, 30 seconds, or 2 minutes). Typically, once the vehicle has come to a complete stop, the vehicle's LAAD system, or another driving system known in the art, may not reengage unless the ignition in the vehicle is cycled from on to off to on again. In some embodiments, the vehicle's LAAD system may not reengage unless a predetermined time interval has passed.

The stages described may be changed in order, have the required response times to cues or prompts shortened, lengthened, or have cues or prompts eliminated entirely within the staged alerting system, depending on the system needs, and conditions within the vehicle or outside the vehicle or both, as determined by vehicle sensors known in the art.

FIG. 1 is a schematic diagram of a vehicle 10 with an automatic vehicle control system. In some embodiments, the driving system is another driving system known in the art. Vehicle 10 (e.g., a car, truck, or another vehicle) may be driven by driver 5. Vehicle 10 may include a steering wheel 20. Steering wheel 20 may include one or more light sources 30. Light source 30 may be within the housing of the steering wheel. In some embodiments, light source 30 may be on the outside surface of the steering wheel. In some embodiments, light source 30 may be extraneous to steering wheel 20, shining a light on steering wheel 20 from a separate location. In some embodiments, an extraneous light source may be on the dashboard of vehicle 10. In some embodiments, light source 30, or an additional light source, may illuminate other components of the vehicle, typically the dashboard. In other embodiments, light source 30, or an additional light, source may illuminate a heads up display and/or the instrument panel behind steering wheel 20. The details for extraneous light source or additional light source may be similar to those of light source 30.

In some embodiments, steering wheel 20 may be illuminated by light source 30 over a given portion of the steering wheel. Typically, the portion illuminated by light source 30 may be between 10 o'clock and 2 o'clock, e.g., between 11 o'clock and 1 o'clock on steering wheel 20. Other ranges may be used.

Light source 30 may be light emitting diodes (LEDs), lasers, incandescent or fluorescent light bulbs or other sources of light as are known in the art. The light source may be an already installed heads up display. In some embodiments, the light emitted from light source 30 may be different colors, patterns or colored patterns. These colors, patterns, or colored patterns typically may represent the current relative level of autonomous driving employed by LAAD system 50, or another driving system known in the art, in vehicle 10. In some embodiments, the colors, patterns, or colored patterns may be indicative of the level of a driver's control over vehicle 10.

Typically steering wheel 20 may be lit or produce light via light source 30 with a distinct color, pattern or colored pattern for each level of autonomy employed by LAAD system 50, or another driving system known in the art. In some embodiments, steering wheel 20 may be lit, or produce light via light source 30, with a distinct color, pattern or colored pattern to indicate to a driver 5 the level of supervisory control necessary to operate vehicle 10 while the vehicle is employing LAAD system 50, or another driving system known in the art.

Typically, LAAD system 50, or another driving system known in the art, is coupled to, and communicates with, light source 30. In some embodiments, a driver prompt system 60 is coupled to, and communicates with, LAAD system 50, or another driving system known in the art, and coupled to, and in communication with, light source 30.

Driver prompt system 60 may include one or more databases 62, which may include, for example, various stages of driver 5 and/or LAAD system 50 controls. Databases 62 may be stored all or partly in one or both of memory 64, long term storage 66, or another device.

A processor or controller 68, typically a central processing unit (CPU), may be a chip or any suitable computing or computational device. Processor or controller 68 may include multiple processors, and may include general-purpose processors and/or dedicated processors such as graphics processing chips. Processor 68 may execute code or instructions, for example, stored in memory 64 or long-term storage 66, to carry out embodiments of the present invention.

Memory 64 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 64 may be or may include multiple memory units.

Long term storage 66 may be or may include, for example, a hard disk drive, a floppy disk drive, a Compact Disk (CD) drive, a CD-Recordable (CD-R) drive, a universal serial bus (USB) device or other suitable removable and/or fixed storage unit, and may include multiple or a combination of such units.

In some embodiments, light source 30 illuminating steering wheel 20 may pulse, flash, or blink at intermittent intervals or at different intensities, or consistent frequencies, to indicate the level of autonomy employed by LAAD system 50, or another driving system known in the art. In some embodiments, light source 30 illuminating steering wheel 20 may pulse, flash, or blink at intermittent intervals or at different intensities or consistent frequencies in conjunction with the operation of another system within vehicle 10, as known in the art.

In some embodiments, light source 30 illuminating steering wheel 20 may pulse or flash at intermittent intervals or at different intensities or frequencies to indicate the level of supervisory control necessary to safely operate the vehicle while vehicle 10 is employing LAAD system 50, or another driving system known in the art. In some embodiments, the colors, patterns, or colored patterns may be indicative of the level of the control driver 5 has over vehicle 10.

In some embodiments, there are four distinct colors, patterns, or colored patterns representing four modes of supervisory control by driver 5 of vehicle 10. Other colors or different numbers of colors may be used.

(1) Disengaged—LAAD system 50, or another driving system known in the art, is not controlling the lateral motion of vehicle 10. Driver 5 is responsible for steering.

(2) Engaged and operating—LAAD system 50, or another driving system known in the art, is controlling the lateral motion of vehicle 10.

(3) Override—LAAD system 50, or another driving system known in the art, has temporarily relinquished control of steering to driver 5, but is prepared to resume control.

(4) Failure—LAAD system 50, or another driving system known in the art, is controlling the lateral motion of vehicle 10 to the best of its ability, but some condition has developed that requires driver 5 to take control immediately.

In some embodiments, there may be other, different, more or fewer modes of supervisory control.

Light source 30 may be typically coupled to LAAD system 50, or another driving system known in the art. In response to a change in the level of autonomy provided by the LAAD system 50, the LAAD system 50, or other system in vehicle 10, may send a signal to light source 30 to change the color, pattern or colored pattern of the light, or frequency and intensity of the light to illuminate steering wheel 20.

In some embodiments, LAAD system 50 and/or driver prompt system 60 may be configured to illuminate steering wheel 20 only while LAAD system 50, or another driving system known in the art, is engaged. In some embodiments, steering wheel 20 may be illuminated even while LAAD system 50, or another driving system known in the art, is not engaged.

Figure 2A:
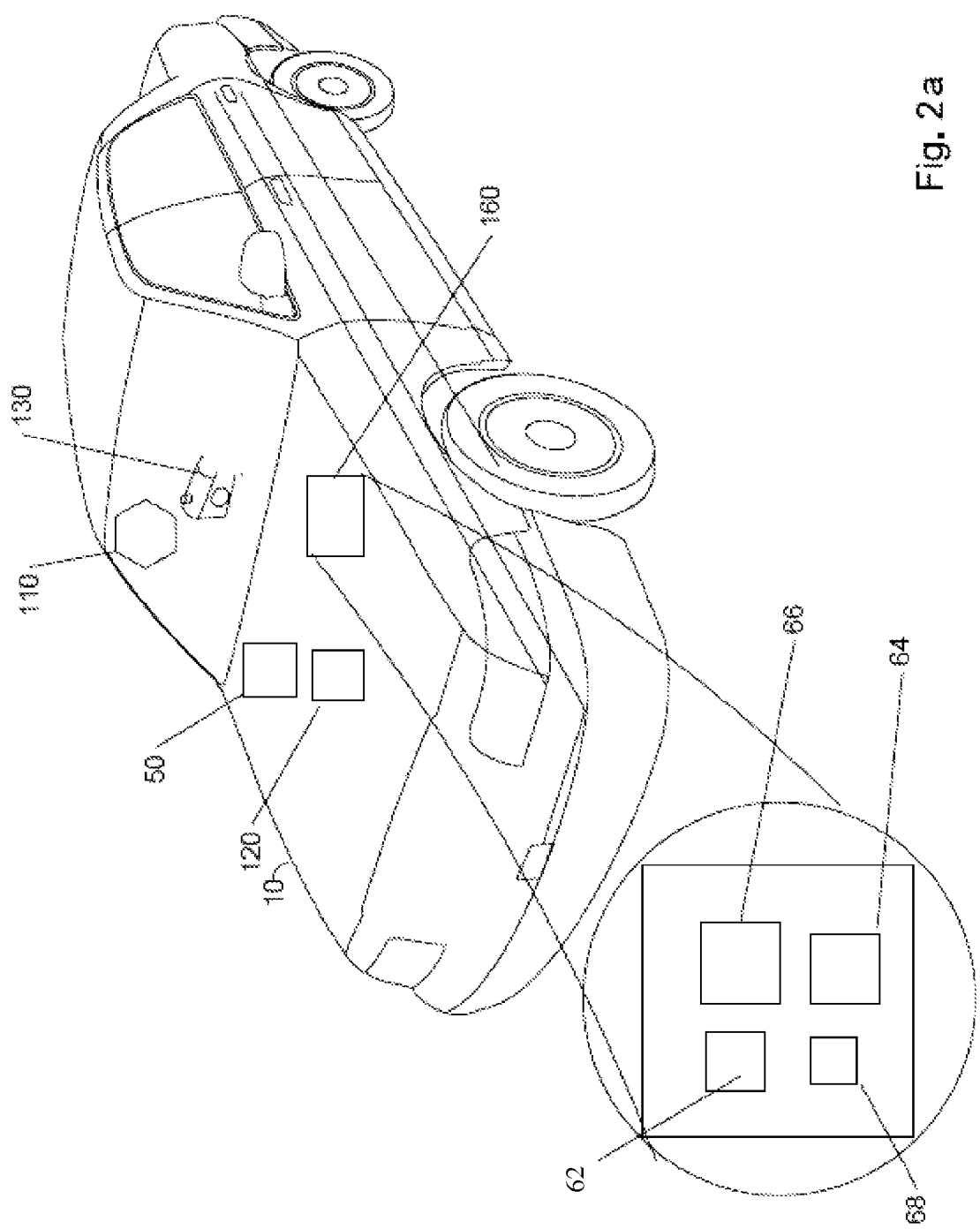
FIG. 2a is a schematic of a vehicle employing a closed-loop driver visual attention management system according to embodiments of the present invention.

FIG. 2a is a schematic diagram of vehicle 10 employing a monitoring system, according to some embodiments of the present invention. Typically, a closed-loop DVAM system may be maintained in a standby state until activated. In some embodiments, the closed-loop DVAM system may include one or more software programs executed by one or more hardware systems in vehicle 10.

Typically, the monitoring system (e.g., a close loop eye gazing monitoring system or another system) may include a control unit 160. Control unit 160 may include a processor or controller 68 and one or more databases 62. One or more databases 62 may include, for example, various scenarios when a driver may need to be cued or prompted. Databases 62 may be stored all or partly in one or both of memory 64, long term storage 66, or another device.

Processor or controller 68 may be, for example, a central processing unit (CPU), a chip or any suitable computing or computational device. Processor or controller 68 may include multiple processors, and may include general-purpose processors and/or dedicated processors such as graphics processing chips. Processor 68 may execute code or instructions, for example, stored in memory 64 or long-term storage 66, to carry out embodiments of the present invention.

Memory 64 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 64 may be or may include multiple memory units.

Long term storage 66 may be or may include, for example, a hard disk drive, a floppy disk drive, a Compact Disk (CD) drive, a CD-Recordable (CD-R) drive, a universal serial bus (USB) device or other suitable removable and/or fixed storage unit, and may include multiple or a combination of such units.

A light source 110, typically a LED, a Light Amplification by Stimulated Emission of Radiation (laser) device, incandescent bulb, florescent bulb, digital light projection, or other light source known in the art, may be configured to flash briefly one or more times, providing an illumination, in response to a signal from control unit 160, which, in turn, may be in response to a signal from a LAAD system 50, or another system, in vehicle 10. In some embodiments of the present invention, there may one or more light sources. Typically, each of potentially several brief flashes of light lasts between 50 and 500 milliseconds. Other ranges may be used. The brief flashes of light, providing an illumination, may be configured to attract the driver's attention without distracting the driver.

In some embodiments of the current invention, the duration of the brief flashes of light providing an illumination may be configured to be short enough in duration or time to be only subtly perceived. In other embodiments, the duration of the brief flashes of light providing an illumination may be sufficient to distract the driver. In some embodiments, the brief flashes may be no longer visible by the time the driver has enough time to react to the brief flash or flashes, for example, in turning the driver's head toward the source, or the perceived source, of the flashes of light.

Typically, control unit 160, and/or LAAD system 50, and/or another system known in the art, in vehicle 10 is configured to send a signal to light source 110 to flash the brief flash of light providing an illumination, such that the light may be visible to the driver as a light, or a reflection of the light, on the windshield. In some embodiments, the light may emit from an already installed heads up display, and reflect on the windshield. In some embodiments, the brief flash of light may be configured to direct the gaze of the driver toward the center of the windshield. In some embodiments, the brief flash of light may be configured to direct the attention of the driver to a direction not in the center of the windshield, in response to a signal from an external vehicle sensor, for example, in response to a vehicle sensor that indicates a foreign object that may be of interest to the driver's supervisory role in controlling the vehicle.

According to some embodiments of the present invention, the closed-loop DVAM system may be configured to perform flashes of a brief light from light source 110 periodically. In some embodiments, the periodic flash of light may be configured to occur after a certain interval of time, independent of data collected from sensors of vehicle 10 regarding internal and/or external conditions.

In some embodiments, the closed-loop DVAM system may be configured to flash a brief light from light source 110 periodically only while LAAD system 50, or another driving system known in the art, is engaged. In some embodiments, the closed-loop DVAM system may be configured to flash a brief light from light source 110, periodically, even while LAAD system 50, or another driving system known in the art, is not engaged.

In other embodiments, the closed-loop DVAM system may be configured to flash a brief light from light source 110, providing an illumination, in response to a foreign object of interest or a change in driving conditions, or a particular direction that may be of interest to the driver's supervisory role in controlling the vehicle. In some embodiments, the closed-loop DVAM system may be configured to flash a brief light from light source 110 in the direction of interest to the driver, as determined by the closed-loop DVAM system, or other systems in vehicle 10, which may be coupled to the closed-loop DVAM system.

Typically, sensors coupled to the closed-loop DVAM system may be configured to determine, via one or more sensors, e.g., sensor 130, as are known in the art, if the driver has looked away from the road for a time period that is calculated by the closed—loop gaze monitoring system, or other driving system known in the art, to be too long. In some embodiments, the time period that is considered too long is dynamically calculated by the closed-loop DVAM system, or other systems in vehicle 10.

In some embodiments, the closed-loop DVAM system may have at least one or more sensors configured to determine if the driver has responded to the prompt, here a brief flash of light, and, in some embodiments, to determine the sufficiency of the driver's response to the brief flash of light.

In some embodiments, the sensor may be coupled to a driver monitoring system 120 and/or control unit 160, which typically includes sensor 130. In some embodiments, sensor 130 is a camera. Sensor 130 may be configured to be directed at the driver's eyes and/or head when the driver is looking forward toward the windshield of the vehicle. Sensor 130 may be configured to be directed at the driver's eyes and/or head when the driver is looking toward the object of interest, as determined by sensors and systems on vehicle 10. Other sensors known in the art that are capable of assessing the driver's gaze or head position may also be part of the driver monitoring system 120. The closed-loop DVAM system may be configured to sense a movement of the driver's head and or eyes in response to the brief flash of light from light source 110, via driver monitoring system 120. In some embodiments, sensor 130 may detect the movement of the driver's head toward the brief flash of light. In response to the detection of the driver's head moving, a signal may be sent to driver monitoring system 120, indicating that the driver has responded to the brief flash of light. If sensor 130 fails to detect the movement of the driver's head in the direction of the flash of light, a signal may be sent to the driver monitoring system 120, and or control unit 160. In response to this signal, the driver monitoring system 120 and/or control unit 160 may be configured to send a signal to light source 110 to flash additional brief flashes of light. In some embodiments, these further flashes of light may be more intrusive or urgent, for example, it may be at a greater intensity or for a longer duration than the original flash of light. The closed-loop DVAM system may determine if the driver has responded to the subsequent prompt, e.g., the more intrusive and/or urgent brief flash of light, and, in some embodiments, to determine if the driver failed to respond to the subsequent brief flash of light. In some embodiments, after the driver has failed to respond to the first brief flash of light, a signal may be sent to the staged alerting system, described with reference to FIG. 4, or other systems associated with vehicle 10.

In some embodiments, the closed-loop DVAM system may be enabled only while LAAD system 50, or another driving system known in the art, is engaged. In some embodiments, the closed-loop DVAM system may be configured to be enabled even while LAAD system 50, or another driving system known in the art, is not engaged.

Figure 2B:
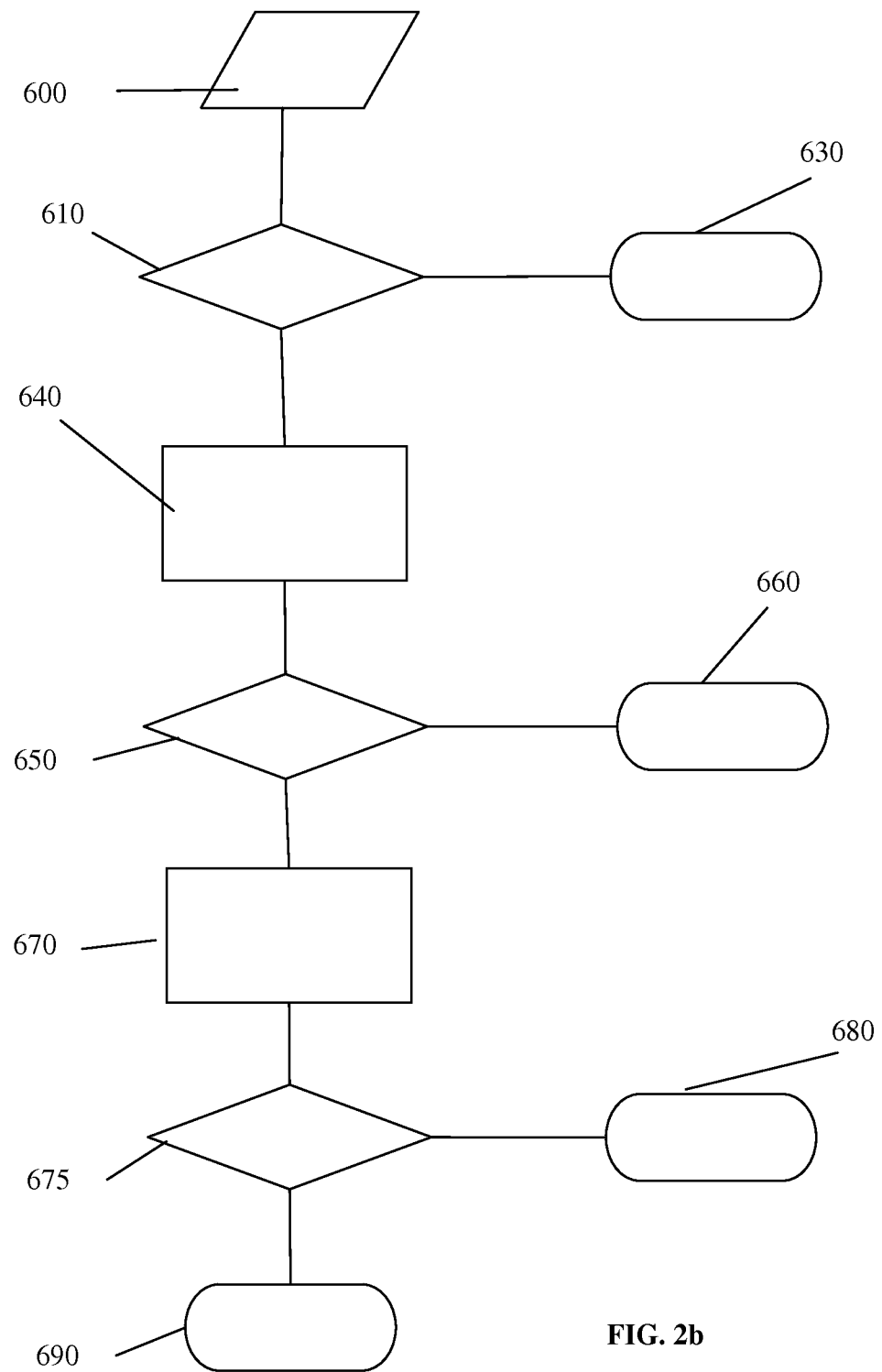
FIG. 2b is a flowchart of a method according to an embodiment of the present invention.

FIG. 2b is a flowchart of a method according to an embodiment of the present invention. The operations in the flow chart may be carried out by a staged alerting system, or by other systems, associated with, or separate from, a vehicle.

Typically, data may be collected by one or more sensors in vehicle 10, as represented by parallelogram 600. In some embodiments, the sensors are similar to sensors 130. The data collected by the sensors typically relates to whether the driver is paying attention or not paying attention to the roadway, or has looked away from a roadway on which vehicle 10 is traveling. In some embodiments, the data collected relates to other instances of driver supervisory control. In some embodiments, the data collected relates to the level of confidence LAAD system 50, or other driving systems known in the art, has with the current conditions as reflected in the data collected by the sensors. As used herein, the level of autonomy employed by a LAAD system or other autonomous driving system may include or take into account the level of confidence that the LAAD has in a particular driving situation. A level of confidence may be an expected reliability of the driving system or an estimate of the level of proficiency of the system. The confidence level may be related to whether the LAAD is encountering new driving conditions or whether the LAAD is controlling the vehicle in an environment that is likely to change.

The closed-loop DVAM system, as described with reference to FIG. 2a, or another system in vehicle 10, determines if the data collected, as represented by parallelogram 600, indicates that driver 5 is not exercising sufficient supervisory control; the determination is depicted by block 610. It may be determined if, given the data, and the confidence level that LAAD system 50, or another driving system as known in the art, has with the current conditions, the supervisory control employed by driver 5 is sufficient; the determination is depicted by block 610.

The closed-loop DVAM system may determine whether or not driver 5 has been looking away from the roadway for too long. This behavior may indicate a lack of supervisory control. In some embodiments, the determination may be related to the confidence level LAAD system 50, or other driving systems known in the art, has with the current conditions.

If the closed-loop DVAM system determines that driver 5 has not been looking away from the roadway for too long, or, in some embodiments, if LAAD system 50, or another driving system known in the art, determines that the supervisory control employed by driver 5 is sufficient, then the closed-loop DVAM system, or other systems known in the art, cycles to stand-by, as depicted by oval 630. If, however, the closed-loop DVAM system determines that driver 5 has been looking away from the roadway for too long, or, in some embodiments, determines that driver 5 is not exercising sufficient supervisory control given the confidence level that LAAD system 50, or another driving system known in the art, has with the current conditions, then the closed-loop eye gaze monitoring system, or another system known in the art, may provide a prompt or signal. For example, a brief flash of light, as described above with reference to FIG. 2a and as depicted in block 640, may be provided.

The closed-loop DVAM system typically may then determine if driver 5 has sufficiently responded to the brief flashes of light (e.g., by paying more attention to the road, by moving his gaze to the road, or other actions), as depicted in diamond 650. In some embodiments, driver 5 has sufficiently responded to the brief flash of light when driver 5 looks toward the light. If the closed-loop DVAM system determines that driver 5 has sufficiently responded to the brief flash of light then the closed-loop DVAM system may cycle to standby, as depicted oval 660. In some embodiments, the closed-loop DVAM system may use sensors, as described above, with reference to parallelogram 600, to determine if the response of driver 5 to the brief flash of light was sufficient.

If the closed-loop DVAM system determines that the driver has not sufficiently responded to the brief flash of light, then the closed loop DVAM system may flash a second brief flash of light, as depicted by block 670. In some embodiments, this second brief flash of light may be more intrusive than the previous brief flash of light, as described earlier with reference to FIG. 2a.

If the closed-loop eye gaze monitoring system determines, as depicted by diamond 675, that the response of driver 5 to the brief flash of light was sufficient, which may be similar to what was described above with reference to diamond 650, then the closed-loop eye gaze monitoring system may cycle to stand-by as depicted by oval 680.

If the closed loop eye gaze monitoring system determines that the response of driver 5 was insufficient, then the closed-loop DVAM system may engage the staged alerting system, as described with reference to FIG. 4, and as depicted by oval 690. While specific series of prompts or cues are described herein, other series of prompts or cues may be used with embodiments of embodiments of the present invention.

Figure 3:
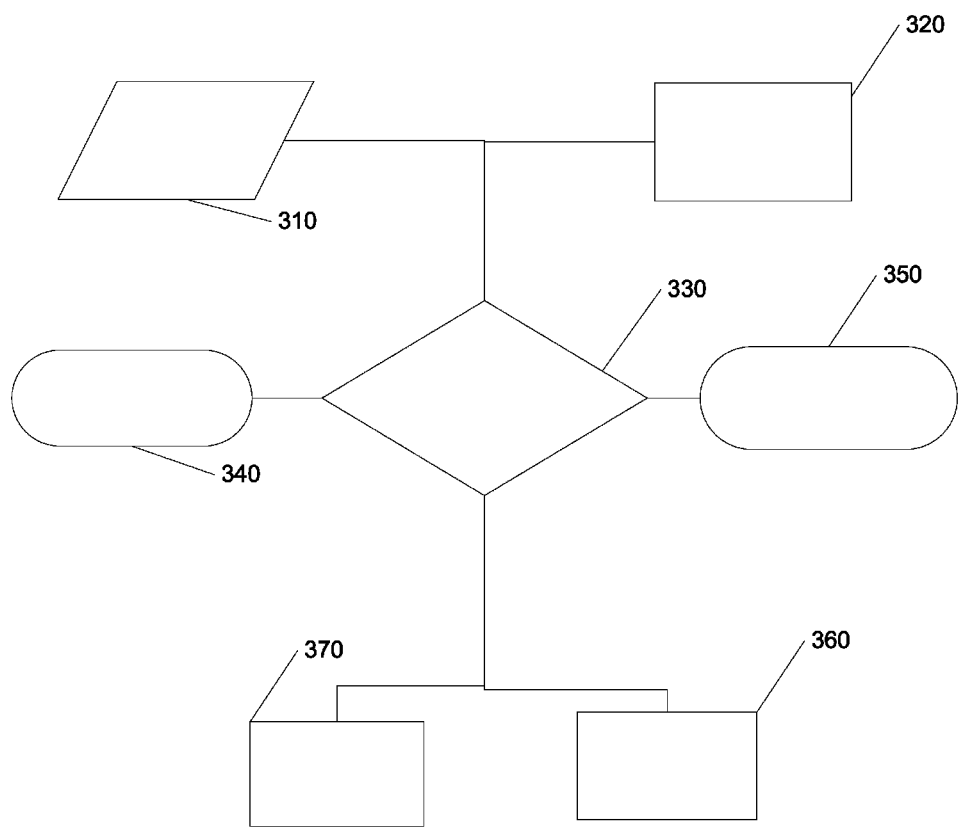
FIG. 3 is a flowchart of a method according to an embodiment of the present invention.

FIG. 3 is a flowchart of a method according to an embodiment of the present invention. The operations in the flow chart may be carried out by a control unit executing software as described with reference to FIGS. 1 and 2. In other embodiments, the operations of the flow chart may be carried out by a LAAD system, as described with reference to FIGS. 1 and 2, a convenience message system, or by other systems associated with, or separate from, vehicle 10.

Typically, the convenience message system may be maintained in a standby state until activated. In some embodiments, the convenience message system may include one or more software programs executed by one or more hardware systems in vehicle 10.

In some embodiments, a convenience message system may be enabled only while a LAAD system, or another driving system known in the art, is engaged. In some embodiments, a convenience message system may be configured to be enabled even while the LAAD system, or another driving system known in the art, is not engaged.

One or more sensor(s), for example, sensors similar to sensor 130, as described with reference to FIG. 2a, may be coupled to, or associated with, the vehicle 10. Sensors may include a computer vision sensor (e.g., a camera), light detection and ranging RADAR (LIDAR) systems, or laser RADAR (LADAR) systems. Both RADAR systems typically employ optical remote sensing technologies that can measure the distance to a target, or other properties of a target, by illuminating the target with light, typically, pulses from a laser. The sensors may also include one or more RADAR systems, an imager, or other remote sensing devices. The sensors may obtain data allowing a system within vehicle 10, e.g., a LAAD system, or other system known in the art, to determine the relative location of vehicle 10 with respect road features, for example, lane markers(s), road shoulder(s), median barrier(s), edge of the road and other objects or features. The camera may, for example, measure lane offset, heading angle, lane curvature and/or other information (e.g., speed, acceleration, yaw-rate, other driver input etc.) and provide the information to vehicle 10.

Vehicle 10 may further include one or more devices or sensors to measure vehicle steering measurements, vehicle steering conditions, vehicle steering parameters, vehicle dynamics, driver input, or other vehicle related conditions or measurements. The vehicle dynamics measurement device(s) may include one or more steering angle sensor(s) (e.g., connected to steering wheel and/or another component of the steering system) and/or steering torque sensor(s) (e.g., a torsion bar, torsion sensor, torquemeter, torque transducer, or other device). Steering torque sensor(s) may be connected to or associated with a steering wheel, a steering column, steering rack and pinion, a vehicle axle, and/or another component of the steering system. The vehicle dynamics measurement device(s) may also include one or more accelerometer(s), speedometer(s), wheel speed sensor(s), inertial measurement unit(s) (IMU), or other devices. The vehicle dynamics measurement device(s) may measure vehicle dynamics conditions or driver input including steering angle, steering torque, steering direction, lateral (e.g., angular or centripetal) acceleration, longitudinal acceleration, yaw-rate, lateral and longitudinal velocity, speed, wheel rotation, and other vehicle dynamics characteristics of vehicle 10. Other sensors known in the art, including both internal and external sensors, may also be coupled to vehicle 10.

In some embodiments, the convenience message system, may, in response to the cumulative data from these and/or sensors known in the art, as depicted in operation 310, or in response to other systems associated to vehicle 10, determine that the convenience message system should engage, as depicted in operation 330. The engagement of the convenience message system may be configured to confirm the supervisory role of the driver of vehicle 10—e.g., to confirm that the driver is supervising the operation of the vehicle and/or paying attention. In some embodiments, the convenience message system may be configured to determine that the convenience message system should engage, as depicted in operation 330, in response to cumulative data from these sensors, or in response to other systems associated to vehicle 10, as depicted in data operation 310, to change the supervisory role of the driver of vehicle 10. If the data from the sensors, or other systems associated to vehicle 10, do not necessitate the engagement of the convenience message system, as depicted in operation 330, then the convenience message system may not engage, as depicted in operation 340, returning to a standby mode.

In some embodiments, the convenience message system may engage, as depicted in operation 330, if the system determines that a given time interval, as depicted in operation 320, between the current time and the last engagement of the convenience message system is sufficient. The time interval may be between 2 and 10 minutes. If the time interval, as depicted in operation 320, is insufficient, then the convenience message system may not engage, as depicted in operation 350, returning, instead, to a standby mode.

Once the convenience message system has been engaged, as depicted in operation 330, the convenience message system, in some embodiments, may produce a prompt or cue message or signal such as an earcon or other tone, as depicted in operation 370. In other embodiments, the system may produce an audio, visual or audiovisual message, as depicted in operation 360. In some embodiments of the invention, the system may produce a tone and/or an audible indication, and an earcon, as depicted in operation 370, and message, as depicted in operation 360. Typically, a message, as depicted in operation 360, may relate to the data from the sensors, as depicted in operation 310, or other vehicle sensors, that the data that was determined by the convenience message system to be sufficient to engage the convenience message system, as depicted in operation 330.

In other embodiments, a message, as depicted in operation 360, may be independent of data from the sensors, as depicted in operation 310, or other vehicle sensors.

In some embodiments, the convenience message system may be part of a closed-loop system. In the closed-loop convenience message system, the system may have feedback sensors to determine if the driver has responded to the prompt. In particular, to determine whether the convenience message system has confirmed and/or changed the supervisory role of the driver. The feedback sensors may include a camera (e.g., sensor 130 in FIG. 2*a*). The sensor may determine, for example, the direction of the driver's gaze. In some embodiments, an interactive instrument panel may determine whether the driver has interacted with the interactive instrument panel and/or other sensors and systems.

In some embodiments, the closed-loop convenience message system may have feedback sensors in vehicle 10 to determine whether the driver has responded to the prompt and/or changed the driver's supervisory role in response to an audio prompt or earcon, as depicted in operation 370 and/or message, as depicted in operation 360, of the convenience message system. The feedback sensors may include sensors that can determine driver interaction with primary control systems in vehicle 10, including, but not limited to, the steering wheel, accelerator, and brake pedal.

Figure 4:
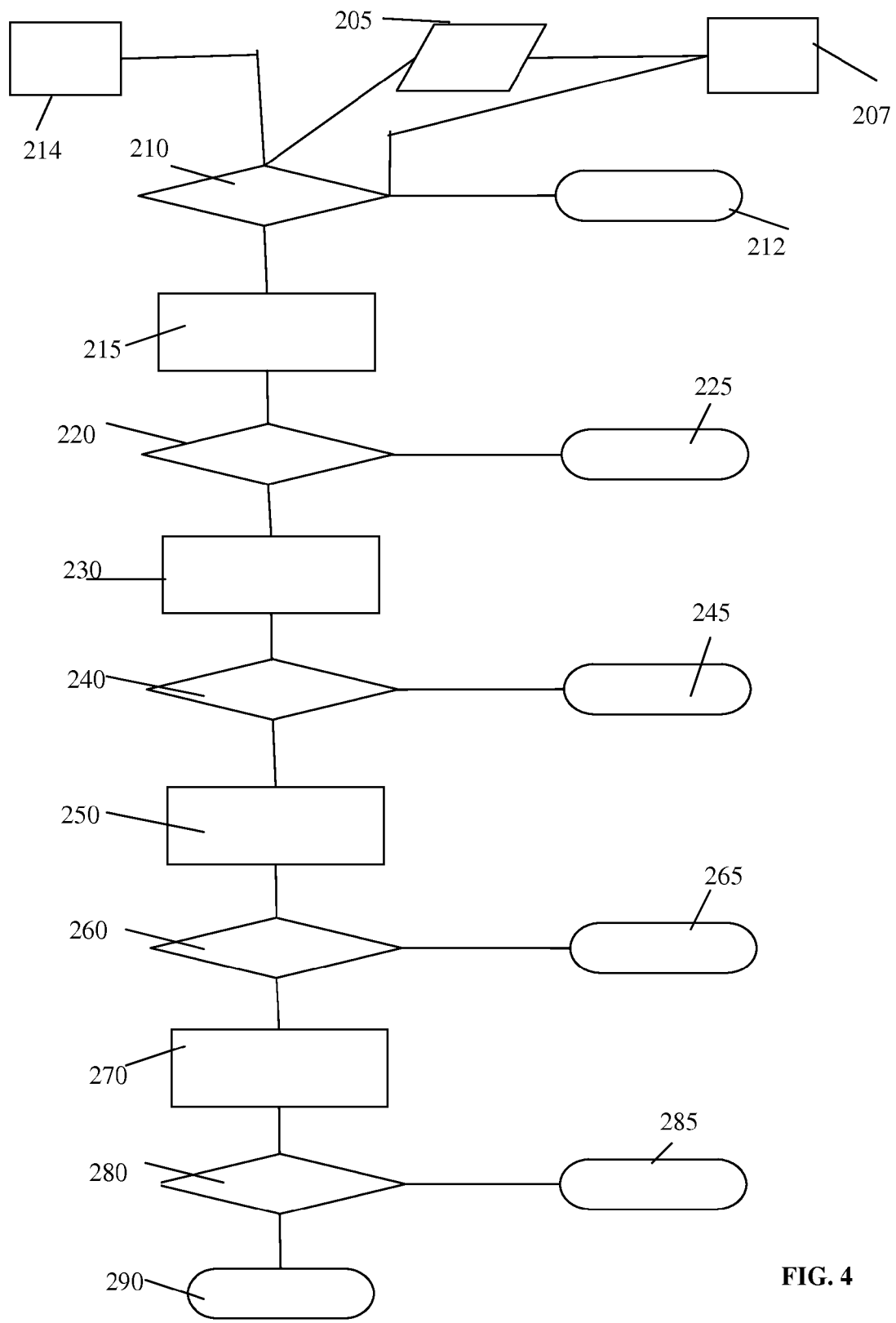
FIG. 4 is a flowchart of a method according to an embodiment of the present invention; and, FIG. 5 is a flowchart of a method according to an embodiment of the present invention.

FIG. 4 is a flowchart of a method according to an embodiment of the present invention. The operations in the flow chart may be carried out by a staged alerting system, or by other systems, associated with, or separate from, vehicle 10. Typically, the staged alerting system may be maintained in a standby state until activated. In some embodiments, the staged alerting system may be executed over one or more hardware and/or software systems in vehicle 10.

In some embodiments, the staged alerting system may be enabled only while a LAAD system, or other driving system as known in the art, is engaged. In some embodiments, the staged alerting system may be configured to be enabled even while the LAAD system, or other driving system as known in the art, is not engaged.

In some embodiments of the present invention, data from one or more of a vehicle's sensors, as described above in reference to FIG. 3, or other vehicle sensors as known in the art, may be collected and measured as depicted in operation 205. The decision to initiate the staged alerting system is determined by the staged alerting system, as depicted in operation 210, in response to the staged alerting system determining the sufficiency of sensor data collected in operation 205, or alternatively, in response to data collected by other systems, and/or sensors associated with vehicle 10. Typically, if it is determined by the staged alerting system, as depicted in operation 210, that the stage alerting system need not be initiated, the staged alerting system may cycle back to a standby mode, as depicted in operation 212. If it is determined, by the staged alerting system, as depicted in operation 210, that the sensor data collected, as depicted in operation 205, is sufficient for the staged alerting system to be initiated, the staged alerting system may provide an attention cue or prompt to the driver of the vehicle. The staged alerting system may, for example, initiate when it detects that the driver has not exercised sufficient supervisory control over the vehicle. This detection may be based on the driver's behavior or biological factors. The driver's behavior being detected may include head movement, eye movement, verbal actions, body movement, and interactions with the vehicle. The driver's behavior may further include interactions with their smart phone or other device, indicating that the driver is not exercising sufficient supervisory control.

In some embodiments, sufficiency may be determined by whether the information necessitates that the driver change or maintain the driver's supervisory role in operating vehicle 10. In some embodiments, the driver may need to change the driver's supervisory role in operating vehicle 10 in instances when the staged alerting system, or other vehicle systems known in the art, determine that the driver, using a LAAD system, or other driving system known in the art, is paying insufficient attention to the operation of the vehicle. Typically, the sensors, coupled to a vehicle driving system known in the art, may determine the level or risk related to the current supervisory control of the vehicle and/or the driver, and calculate what level of driver supervision is required given that risk as depicted in block 207. In some embodiments, the data for this calculation may come from the sensor data collected, as depicted in operation 205. This level of driver supervision required may be related to the time the driver may look away from the road before being prompted by the staged alerting system or another vehicle driving system known in the art. In some embodiments, the sensors may indicate an exception, hazardous situation, or an obstacle in the path of the vehicle and may prompt driver 5 via the staged alerting system or another vehicle driving system known in the art. In some embodiments, the level of driver supervision required or the level of sufficient supervisory control may be adjustable by the driver.

In some embodiments, the driver may need to change the driver's supervisory role in operating vehicle 10 in instances when the staged alerting system, or other vehicle systems known in the art, determine that there is a decision regarding current or upcoming driving situations that the driver may want to make. In some embodiments, the driver may need to change the driver's supervisory role in operating vehicle 10 in instances when the staged alerting system, or other vehicle systems, determine that the LAAD system, or other driving systems known in the art, is not confident in its ability to continue to control some aspect of the vehicle's motion due to some aspect of the current or upcoming driving situation that is outside of its scope of capability. In some embodiments, the staged alerting system, or other vehicle systems, may determine that the LAAD system, or other driving systems known in the art, is experiencing a fault or lacks the necessary capabilities to continue to drive the vehicle. Driving situations that are outside of the scope of the capability of a LAAD system, or other driving systems known in the art, may include current lane ending, current lane exits the freeway, and current lane splits to include an exit on the right or left, current lane forks. A LAAD system, or other driving systems known in the art, may also not be confident in a situation wherein a vehicle is being followed, the followed vehicle traveling at a speed significantly below the current cruise set speed, and as a result of the employment of an adaptive cruise control system, the driver's vehicle has been traveling at this lower speed for a particular time period.

In some embodiments of the current invention, a time interval may be calculated, as depicted by operation 214. If the time interval is determined to be sufficient by operation 210, then the staged alerting system may be engaged. If the time interval is determined to be insufficient, then typically, the staged alerting system may cycle back to a standby state. The attention cue or prompt, as depicted by operation 215, may be a light providing illumination similar to that used with the closed loop DVAM. Further, the interaction between the prompt and the driver response, as depicted in operation 220, may be similar to that used with the DVAM, described herein.

As depicted in operation 220, the sufficiency of the driver response to the attention cue or prompt may determine whether the staged alerting system cycles back to a standby state, as depicted in operation 225. If the driver's response is insufficient, or in some embodiments, unable to be determined, as determined by the sensors in the vehicle, the staged alerting system may continue attempting to alert the driver via a non-visual cue or prompt, as depicted in operation 230.

A non-visual cue or prompt, as depicted as operation 230, may be a haptic cue or prompt. Typically, the haptic cue or prompt may be from the driver's seat or steering wheel. Haptic cues or prompts may include shaking or vibrating the seat or the steering wheel or both. Other haptic cues or prompts known in the art may also be used. In some embodiments, the driver's seat may be equipped with vibrating motors, and/or other haptic inducing mechanics that are known in the art. Typically the haptic inducing mechanics may cause the seat to shake, pulse, vibrate, or another haptic inducement that is known in the art. In some embodiments, the seat may increase lumbar support of the driver, causing the driver to maintain an alert position. In some embodiments, the steering wheel or steering column, or both, may be equipped with vibrating motors, and/or other haptic inducing mechanics that are known in the art, that may cause the steering wheel to shake, pulse, vibrate, or another haptic inducement that is known in the art. In some embodiments, the gear shifter may be equipped with vibrating motors, and/or other haptic inducing mechanics that are known in the art. These haptic inducing mechanics may cause the gear shifter to shake, pulse, vibrate, or another haptic inducement that is known in in the art. Other devices in the vehicle may be equipped with other haptic inducing mechanics, such as the brake pedal pulsing or vibrating, for example.

In some embodiments, a non-visual cue or prompt may include a verbal cueing or messaging system, including OnStar or other on-vehicle voice system. The verbal messaging system may inform the driver of external or internal driving conditions, or may prompt the driver to interact with the vehicle or take notice of a part of the vehicle. Sensors or a sensing system may detect a voice response to the verbal messaging system or other interactions. The sensing system may detect and determine the content of the driver's voice response or detect changes in the driver's speech patterns.

In some embodiments, the staged alerting system may also, in addition to the haptic cue or prompt, or instead of the haptic cue or prompt, provide an audible or other non-visual cue or prompt, as are known in the art. Typically, the audible cue or prompt may be generated by the vehicles speakers. In other embodiments, the audible cue or prompt may be generated by other sources, e.g., a Bluetooth coupled cellular telephone.

As depicted in operation 240, the sufficiency of the driver response to the non-visual cue or prompt may be used to determine whether the staged alerting system cycles back to a standby state, as depicted in operation 245. If the driver's response is determined to be insufficient, or in some embodiments, unable to be determined, as determined by sensors in the vehicle, the staged alerting system may continue attempting to alert the driver via, for example, a second prompt, e.g., a speech cue or prompt, as depicted in operation 250. The staged alerting system may further change the operation of the LAAD system, or other driving system known in the art, such that it may not reengage unless the ignition is cycled. In other embodiments, the LAAD system, or other driving system known in the art, may not reengage for a given period of time as determined by the staged alerting system.

Typically, operation 250 involves a speech cue or prompt, or another form of audible cue or prompt, including an earcon. The speech cue or prompt may be similar to the convenience message system as described hereinabove with reference to FIG. 2a. In some embodiments, the speech cue or prompt may be selected from a pre-set list of phrases configured to elicit a response from the driver of the vehicle, but independent of the road or driving conditions. In some embodiments, the speech cue or prompt may be selected from a list of phrases configured to confirm that the driver wishes to maintain the driver's current level of supervisory control. In some embodiments, the speech cue or prompt may be selected from a list of phrases configured to determine whether the driver wishes to change the current level of supervisory control. In some embodiments, the speech cue or prompt may be configured to be heard by other passengers in the vehicle.

As depicted in operation 260, the sufficiency of the driver response to the speech cue or prompt may determine whether the staged alerting system cycles back to a standby state, as depicted in operation 265. If the driver's response is insufficient, or in some embodiments, unable to be determined, as determined by sensors in the vehicle, the staged alerting system may continue attempting to alert the driver via a vehicle speed reduction, as depicted in operation 270. If the driver's response is determined to be insufficient, or in some embodiments, unable to be determined, as determined by sensors in the vehicle, the staged alerting system may change the operation of the LAAD system, or other driving system known in the art, such that it may not reengage unless the ignition is cycled. In other embodiments, the LAAD system, or other driving system known in the art, may not reengage for a given period of time as determined by the staged alerting system.

In some embodiments, operation 270 may involve the staged alerting system disengaging the normal longitudinal control systems in vehicle 10. In some embodiments, operation 270 may further involve the staged alerting system slowing the vehicle. The reduction in speed can be limited, for example, to between 10 and 30 miles per hour below the prevailing traffic speed. Other ranges may be used.

In some embodiments, the staged alerting system may be configured to move the vehicle to the side of the road and stop, and/or to pulse the brakes as the vehicle is slowed.

As depicted in operation 280, the sufficiency of the driver response to the speech cue or prompt may determine whether the staged alerting system cycles back to a standby state, as depicted in operation 290. If the driver's response is insufficient, or in some embodiments, unable to be determined, as determined by sensors in the vehicle, the staged alerting system may bring the vehicle to a complete stop, as depicted in operation 285.

In some embodiments, once the vehicle has pulled over or stopped, as depicted in operation 285, the LAAD system, or other driving system known in the art, may not reengage unless the ignition is cycled. In other embodiments, the LAAD system, or other driving system known in the art, may not reengage for a given period of time as determined by the staged alerting system.

Figure 5:
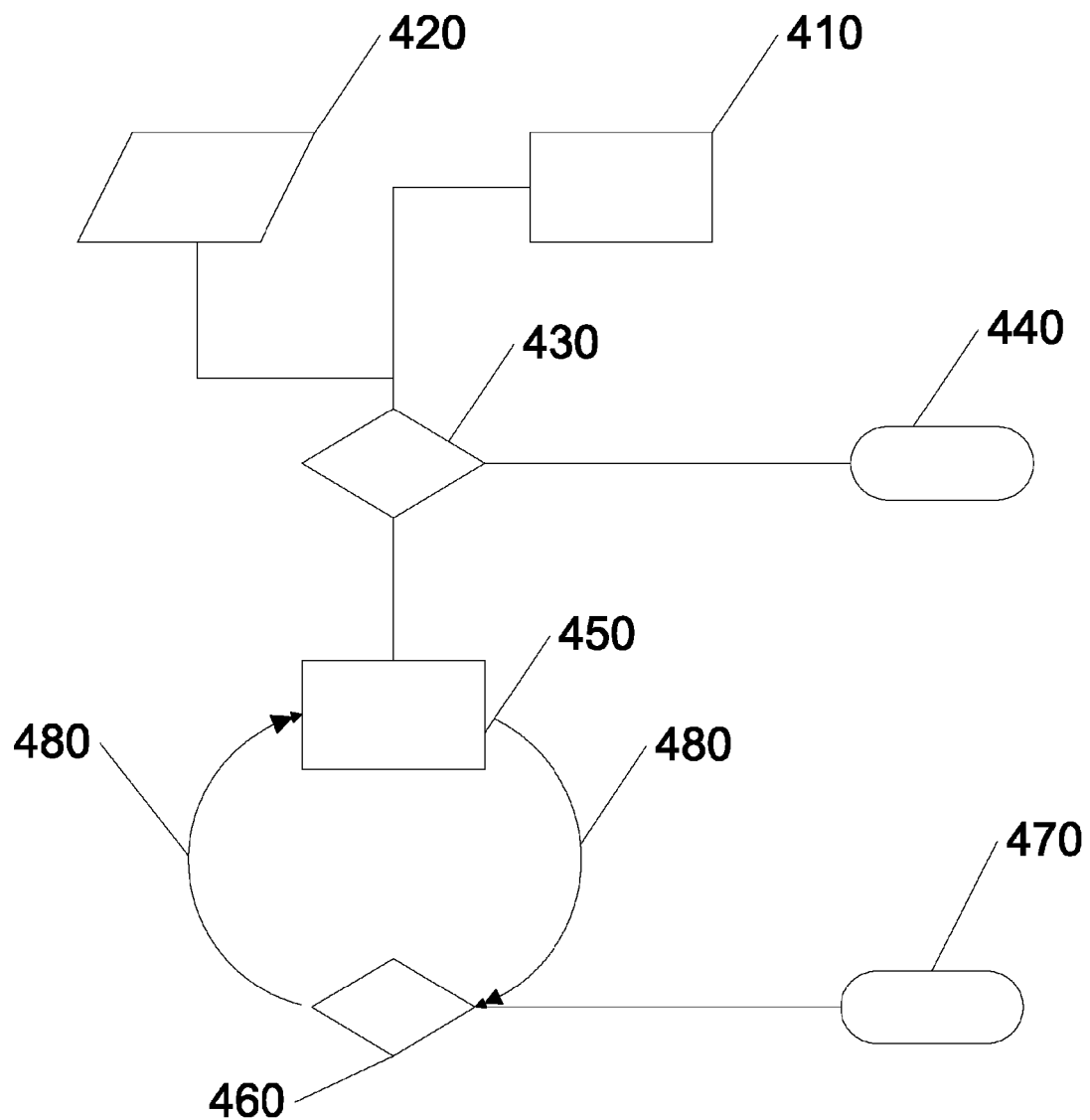

FIG. 5 is a schematic illustration of an embodiment of the present invention. Typically, a driver interaction system, or another vehicle system known in the art, is on standby in vehicle 10. A system, e.g., LAAD 50, or another driving system known in the art, signals driver 5, as depicted by block 410. In some embodiments, LAAD system 50, or another driving system known in the art, monitors driver 5, and or the surroundings of driver 5, inside and/or outside of vehicle 10, as depicted by data collected in parallelogram 420. In some embodiments, driver 5 is monitored and signaled in response to data collected.

The LAAD system 50, or another driving system known in the art, determines, as depicted in diamond 430, whether to activate driver interaction system, based on data collected, as depicted in parallelogram 420 or, in some embodiments, based on the response of driver 5 to the signaling driver 5 by the LAAD system, or another driving system known in the art, as depicted in block 410, or in some embodiments, both.

If the LAAD system 50, or another driving system known in the art, determines that the driver interaction system does not need to be activated, then the driver interaction system cycles back to standby, as depicted in oval 440.

If the LAAD system 50, or another driving system known in the art, determines that a driver interaction system needs to be activated, then the driver interaction system may be activated and may send a signal (e.g., a prompt, cue, light, etc.) to driver 5, as depicted in block 450. In some embodiments, the signals sent to driver 5 may be increasingly insistent, strong, or intrusive, depending on how many times it has been determined by the driver interaction system, or another system in vehicle 10, that the driver is not paying attention, is not supervising the on board system, or is not responding to the signal.

In some embodiments, driver interaction system, or another system in vehicle 10, determines the nature of the signal to driver 5 based on how long driver 5 has not been paying attention, is not supervising the on board system, or is not responding to the signal. In some embodiments, the driver interaction system, or another system in vehicle 10, sends a further intrusive signal to driver 5, this signal depicted in block 450, based on either how long or how many times it has been determined by the driver interaction system, or another system in vehicle 10, that driver 5 is not paying attention, or both.

The driver interaction system determines whether the response of driver 5 to the signal is sufficient (e.g., it is determined that the driver is supervising the on board system, or is responding to the signal), as depicted in diamond 460. If the driver interaction system, or another driver system known in the art, in vehicle 10 determines that the response of driver 5 to the signal is sufficient, then the driver interaction system, or another system known in the art, cycles back to standby, as depicted by oval 470. If the driver interaction system determines that the response of driver 5 to the signal is insufficient (e.g., the driver is not supervising the on board system, or is not responding to the signal), then the driver interaction system, or another system known in the art, may send a further intrusive signal to driver 5, wherein the further intrusive signal may be increasingly insistent, strong, or intrusive, depending on how many times it has been determined that driver 5 is not paying attention, or how long driver has not been paying attention, as depicted in block 450. Arrows 480 depict this multiple iteration feedback loop: the driver interaction system determines whether the response of driver 5 to an earlier signal is sufficient, as depicted in diamond 460. If the driver interaction system determines that the response of driver 5 to the signal is sufficient, then the driver interaction system may cycle back to standby, as depicted by oval 470. If the driver interaction system determines that the response of driver 5 to the signal is insufficient, then the driver interaction system may send a further intrusive signal to driver 5, where the signal may be increasingly insistent, strong, or intrusive, depending on how many times it has been determined driver 5 is not paying attention, or how long driver 5 has not been paying attention, as depicted in block 450.

Figure 6:
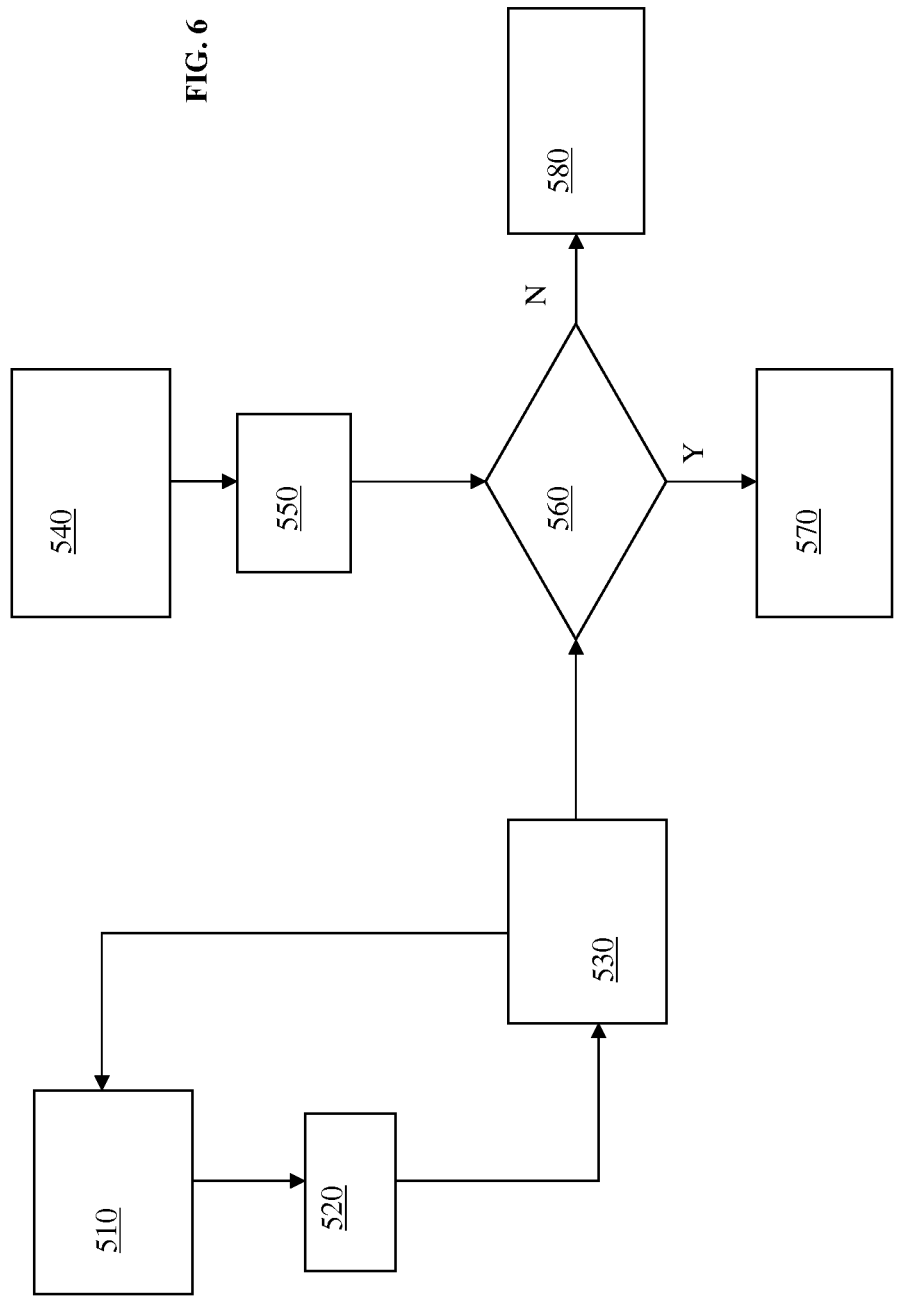
FIG. 6 is a flowchart of a method according to an embodiment of the present invention.

FIG. 6 is a flowchart illustration of a convenience messaging system used in conjunction with a DVAM system, according to an embodiment of the invention. A convenience messaging system may display or provide a convenience message 510 that includes information on items of interest to a driver. The items of interest may include traffic information, weather updates, or nearby destinations. The convenience message may optionally request an acknowledgement or response from the driver. The request may be general or specific, such as requesting the driver to glance in the direction of the convenience message, for example. The driver may respond 520 to the convenience message either by acknowledging the request in the convenience message, or by naturally responding to the information in the message. For example, the driver may grip the steering wheel tighter, turn off the radio, or nod off the radio, or nod his or her head. Sensors may detect such behavior, including any other body movements or vehicle interactions. A processor in the convenience messaging system may determine an attentive or affirmative response from the driver, based on the detected behaviors in the driver's response 520 to the convenience message. Depending on the rules programmed into the system, the processor may determine that the response to the convenience message should be deemed an attentive response. In another example, the processor may determine that the attentive response should not include those behaviors. Over several responses to the conveniences message, e.g., several cycles of providing a convenience message and detecting a response, the processor may use machine learning techniques or algorithms to determine the characteristics of an attentive response. For example, the system may learn that certain kinds of convenience message that describe traffic cause the kind of behavior that should be deemed attentive, but the system may learn that convenience message describing the location of rest stops do not elicit the same response, and the behavior should be excluded from an attentive response.

In some embodiments, a DVAM system may incorporate the attentive response 530 determined by the convenience messaging system as a check or correction in its system for determining whether a driver is responding to its prompts or whether the driver is exercising supervisory control over a vehicle. The DVAM system, which may be part of an autonomous driving system, may provide prompts to the driver 540. The DVAM system may detect the driver's response (or lack of response) to the prompt 550. The DVAM system may detect behaviors or characteristics of the driver that are similar to the ones detected by the convenience messaging system. The DVAM system may determine whether a driver is exercising supervisory control of a vehicle, based on the detected response of the driver and the determined attentive response in step 530. The determination may be based on whether the detected response of the driver in step 550 and the determined attentive response are similar. If they are not similar, the DVAM system may determine 580 that the driver is not supervising the vehicle adequately. If they are similar, the DVAM system may determine 570 that the driver is exercising adequate control over the vehicle. The DVAM system may continue to provide further prompts or provide more intrusive alerts, as described in other embodiments of the invention. Since, the convenience messaging system acts as a diagnostic check for the DVAM system, the convenience message may be provided with less frequency than the prompts of the DVAM system. For example, the convenience message may be provided every 3-5 minutes, while the prompts may be provided every 30-50 seconds. Other frequencies may be used.

In some embodiments of the current invention, the specifics and details of the staged alerting system may be optimized to improve driver performance. In some embodiments, the stages and/or their order of the stages in the staged alerting system may also be adjusted or removed entirely depending on data collected by sensors internal and external to the vehicle.

Embodiments of the present invention may include apparatuses for performing the operations described herein. Such apparatuses may be specially constructed for the desired purposes, or may include computers or processors selectively activated or reconfigured by a computer program stored in the computers. Such computer programs may be stored in a computer-readable or processor-readable non-transitory storage medium, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions. It may be appreciated that a variety of programming languages may be used to implement the teachings of the invention, as described herein. Embodiments of the invention may include an article such as a non-transitory computer or processor readable non-transitory storage medium, such as for example a memory, a disk drive, or a USB flash memory encoding, including or storing instructions, e.g., computer-executable instructions, which when executed by a processor or controller, cause the processor or controller to carry out methods disclosed herein. The instructions may cause the processor or controller to execute processes that carry out methods disclosed herein.

Features of various embodiments discussed herein may be used with other embodiments discussed herein. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A closed-loop diagnostics method, comprising:
providing, by a processor in a vehicle, a convenience message to alert a driver of an item of interest to the driver;
detecting, by a sensor, the driver's response to the convenience message;
determining, based on the driver's response, the characteristics of an attentive response from the driver; and
utilizing the determined characteristics of the attentive response in a driver attention management system.

2. The method of claim 1, wherein utilizing the characteristics of the attentive response in a driver attention management system comprises diagnosing sensor error in the driver attention management system, based on the characteristics of the attentive response.

3. The method of claim 1, comprising requesting a response from the driver after the convenience message is provided.

4. The method of claim 1, wherein utilizing the determined characteristics of the attentive response in a driver attention management system comprises:
providing a prompt to the driver;
detecting the driver's response to the prompt; and
determining whether the driver exercises sufficient supervisory control of the vehicle based on the driver's response to the prompt and the determined characteristics of the attentive response.

5. The method of claim 4, wherein determining whether the driver exercises sufficient supervisory control of the vehicle comprises determining whether the driver's response to the prompt is similar to the determined characteristics of the attentive response.

6. The method of claim 4, wherein the convenience message is provided less frequently than the prompt to the driver.

7. The method of claim 1, wherein detecting the driver's response to the convenience message comprises detecting behavioral characteristics of the driver, including head movement, eye movement, body movement, or interactions with the vehicle.

8. The method of claim 1, wherein providing a convenience message to alert a driver comprises providing at least one of: an audio message, visual message, and an audiovisual message.

9. The method of claim 1 wherein the item of interest to the driver comprises information on at least one of: an external driving condition and points of interest in the vehicle's vicinity.

10. A closed-loop diagnostics system, comprising:
a processor, on a vehicle, to provide a convenience message to alert a driver of an item of interest to the driver;
a sensor to detect the driver's response to the convenience message;

wherein the processor is further to:
  determine, based on the driver's response, the characteristics of an attentive response from the driver; and
  utilize the determined characteristics of the attentive response in a driver attention management system.

11. The system of claim 10, wherein the processor is to utilize the characteristics of the attentive response in a driver attention management system by diagnosing sensor error in the driver attention management system, based on the characteristics of the attentive response.

12. The system of claim 10, wherein the processor is to utilize the characteristics of the attentive response in a driver attention management system by:
  providing a prompt to the driver;
  detecting the driver's response to the prompt; and
  determining whether the driver exercises sufficient supervisory control of the vehicle based on the driver's response to the prompt and the determined characteristics of the attentive response.

13. The system of claim 12, wherein the processor is to determine whether the driver exercises sufficient supervisory control of the vehicle by determining whether the driver's response to the prompt is similar to the determined characteristics of the attentive response.

14. The system of claim 12, wherein the processor is to provide a convenience message less frequently than the prompt to the driver.

15. The system of claim 10, wherein the sensor is to detect the driver's response to the convenience message by detecting behavioral characteristics of the driver, including head movement, eye movement, body movement, or interactions with the vehicle.

16. An apparatus, comprising:
  a convenience messaging system to:
    alert a driver of an item of interest to the driver;
    detect the driver's response to the convenience message;
    determine an attentive driver response based on the driver's response to the convenience message;
  a driver attention management system to determine whether the driver exercises sufficient supervisory control of a vehicle, based on the determined attentive driver response.

17. The apparatus of claim 16, wherein the driver attention management system is adapted to diagnose sensor error in the driver attention management system, based on the determined attentive response.

18. The apparatus of claim 16, wherein the driver attention management system is to:
  provide a prompt to the driver;
  detect the driver's response to the prompt; and
  determine whether the driver exercises sufficient supervisory control of the vehicle based on whether the driver's response to the prompt is similar to the determined attentive driver response.

19. The apparatus of claim 16, wherein the convenience messaging system to alert a driver of an item of interest to the driver by providing at least one of: an audio message, visual message, and an audiovisual message.

20. The apparatus of claim 16, wherein the convenience messaging system is to detect the driver's response to the convenience message by detecting behavioral characteristics of the driver, including head movement, eye movement, body movement, or interactions with the vehicle.

* * * * *